United States Patent
Tan et al.

(10) Patent No.: US 7,656,536 B2
(45) Date of Patent: Feb. 2, 2010

(54) FIBER-OPTIC ASSAY APPARATUS BASED ON PHASE-SHIFT INTERFEROMETRY

(75) Inventors: Hong Tan, San Jose, CA (US); Yushan Tan, Shanghai (CN); Krista Leah Witte, Hayward, CA (US); Greg L. Carricato, San Jose, CA (US); Scott Lockard, Los Gatos, CA (US)

(73) Assignee: Fortebio, Inc., Menlo Park, CA (US)

( * ) Notice: Subject to any disclaimer, the term of this patent is extended or adjusted under 35 U.S.C. 154(b) by 0 days.

(21) Appl. No.: 11/957,340

(22) Filed: Dec. 14, 2007

(65) Prior Publication Data

US 2008/0144039 A1    Jun. 19, 2008

Related U.S. Application Data

(63) Continuation of application No. 11/423,671, filed on Jun. 12, 2006, now Pat. No. 7,319,525, which is a continuation-in-part of application No. 10/981,901, filed on Nov. 4, 2004, now Pat. No. 7,394,547.

(60) Provisional application No. 60/518,068, filed on Nov. 6, 2003, provisional application No. 60/558,381, filed on Mar. 31, 2004, provisional application No. 60/690,324, filed on Jun. 13, 2005.

(51) Int. Cl.
    *G01B 9/02* (2006.01)
(52) U.S. Cl. ..................... 356/478; 356/480
(58) Field of Classification Search ............ 356/477, 356/478, 480
    See application file for complete search history.

(56) References Cited

U.S. PATENT DOCUMENTS

| | | |
|---|---|---|
| 4,830,451 A | 5/1989 | Stone |
| 5,301,001 A | 4/1994 | Murphy et al. |
| 5,359,405 A | 10/1994 | Andrews |
| 5,422,970 A | 6/1995 | Miller et al. |
| 5,425,039 A | 6/1995 | Hsu et al. |
| 5,452,087 A | 9/1995 | Taylor et al. |
| 5,528,367 A | 6/1996 | Putnam et al. |
| 5,594,819 A | 1/1997 | Narendran et al. |
| 5,606,170 A | 2/1997 | Saaski et al. |
| 5,647,038 A | 7/1997 | Minden et al. |
| 5,682,237 A | 10/1997 | Belk |

(Continued)

FOREIGN PATENT DOCUMENTS

WO    WO 2004/025282 A    3/2004

OTHER PUBLICATIONS

Boiarski, A. et al., "Integrated-Optic Biosensor", SPIE, Fiber Optic Sensors in Medical Diagnostics, vol. 1886, 1993, pp. 15-26.

(Continued)

*Primary Examiner*—Michael A Lyons
(74) *Attorney, Agent, or Firm*—Fenwick & West LLP

(57) ABSTRACT

Apparatus and method for detecting an analyte in a sample based on optical interference. The apparatus includes a light source, detector unit and one or more disposable detector tips. The apparatus also includes an optical coupling assembly that couples light from the source to the detector tips, and from the detector tips to the detector unit.

20 Claims, 11 Drawing Sheets

U.S. PATENT DOCUMENTS

| | | | |
|---|---|---|---|
| 5,701,193 | A | 12/1997 | Vogel et al. |
| 5,732,169 | A | 3/1998 | Riant et al. |
| 5,804,453 | A | 9/1998 | Chen |
| 5,869,835 | A | 2/1999 | Udd |
| 5,982,959 | A | 11/1999 | Hopenfeld |
| 6,055,080 | A | 4/2000 | Furstenau et al. |
| 6,078,706 | A | 6/2000 | Nau et al. |
| 6,139,797 | A | 10/2000 | Suzuki et al. |
| 6,241,397 | B1 | 6/2001 | Bao et al. |
| 6,244,214 | B1 | 6/2001 | Hebrank |
| 6,248,539 | B1 | 6/2001 | Ghadiri et al. |
| 6,254,830 | B1 | 7/2001 | Pivarnik et al. |
| 6,275,628 | B1 | 8/2001 | Jones et al. |
| 6,277,651 | B1 | 8/2001 | Groger et al. |
| 6,281,976 | B1 | 8/2001 | Taylor et al. |
| 6,445,838 | B1 | 9/2002 | Caracci et al. |
| 6,496,618 | B1 | 12/2002 | Fernando et al. |
| 6,539,136 | B1 | 3/2003 | Dianov et al. |
| 6,571,639 | B1 | 6/2003 | May et al. |
| 6,590,665 | B2 | 7/2003 | Painchaud et al. |
| 6,611,334 | B1 | 8/2003 | Fernando et al. |
| 6,661,520 | B1 | 12/2003 | Lin et al. |
| 6,671,055 | B1 | 12/2003 | Wavering et al. |
| 6,687,011 | B1 | 2/2004 | Lee et al. |
| 6,720,177 | B2 | 4/2004 | Ghadiri et al. |
| 6,744,939 | B2 | 6/2004 | Lampert et al. |
| 7,158,225 | B2 | 1/2007 | Tedesco et al. |
| 7,319,525 | B2 * | 1/2008 | Tan et al. .................... 356/478 |
| 2001/0048072 | A1 | 12/2001 | Painchaud et al. |
| 2003/0112443 | A1 | 6/2003 | Hjelme et al. |
| 2004/0022475 | A1 | 2/2004 | Pennington |
| 2004/0186359 | A1 | 9/2004 | Beaudoin et al. |

OTHER PUBLICATIONS

Brecht, A., et al., "Recent Developments in Optical Transducers for Chemical or Biochemical Applications," Sensors and Actuators B, Jan. 1997, pp. 1-7, vol. 38, No. 1-3.

Brecht, A. et al., "Direct Monitoring of Antigen-Antibody Interactions by Spectral Interferometry", Sensors and Actuators, vol. B5, 1992, pp. 96-100.

Brecht, A. et al., "Interferometric Immunoassay in a FIA-System: a Sensitive and Rapid Approach in Label-free Immunosensing", Biosensors & Bioelectronics, vol. 8, 1993, pp. 387-392.

Brecht, A. et al., "Theoretical and Experimental Detectivity of the RIFS—transducer in Affinity-sensing", Biosensors 94, The Third World Congress on Biosensors: Abstracts, Oral Session, Jun. 2, 1994, p. 68.

Cao, L. et al., "Detection of Yersinia Pestis Fraction 1 Antigen With a Fiber Optic Biosensor", Journal of Clinical Microbiology, vol. 33, No. 2, Feb. 1994, pp. 336-341.

Chinese Application No. 200480031823.5 Office Action, Jul. 20, 2007, 16 pages.

Christensen, D. et al., "Analysis of Excitation and Collection Geometries for Plannar Waveguide lmmunosensors," SPIE vol. 1886, Fiber Optic Sensors in Medical Diagnostics, 1993, pp. 2-8.

Davies, R. et al., "An Optical Biosensor System for Molecular Interaction Studies", American Biotechnology Laboratory, Jul. 1993.

Elster J. L.., et al., "Optical Fiber Extrinsic Fabry-Perot Interferometric (EFPI)-Based Biosensors," Biomedical Diagnostic, Guidance, and Surgical-Assist Systems II, Proceedings of the SPIE, 2000, pp. 105-112, vol. 3911.

European Examination Report, EP 04800761.1, Nov. 23, 2007,5 pages.

European Supplementary Search Report, EP 04800761, Mar. 19, 2007,4 pages.

Fabricius, N. et al., "A Gas Sensor Based on an Integrated Optical Mach-Zehnder Interferometer", Sensors and Actyators, vol. B7, 1992, pp. 672-676.

Gauglitz, G. et al., "Observation of Spectral Interferences for the Determination of Volume And Surface Effects of Thin Films", Fresenius Analytical Biochemistry, vol. 341, 1991, pp. 279-283.

Gauglitz, G. et al., "Recent Developments in Optical Transducers for Chemical or Biochemical Applications," Sensors and Actuators B, Jan. 1997, pp. 1-7, vol. 3-39, Elsevier Science S.A., Lausanne, CH.

Hogg, D. et al., "Development of a Fiber Fabry-Perot Strain Gauge", SPIE vol. 1588, Fiber Optic Smart Structures and Skins IV, 1991, pp. 300-307.

Jorgenson, R. et al. "A Novel Surface Plasmon Resonance Based Fiber Optic Sensor Applied to Biochemical Sensing", SPIE, Vol. 1886, 1993, pp. 35-48.

Kimoshita, Y. et al., "Sensing of Herbicide Residues Using Surface Plasmon Resonance Technique", The Third World Congress on Biosensors: Abstracts, 1994, p. 257.

Lin, C. J., "A Novel In-Vitro and In-Situ Immunoassay Biosensor Based on Fiber-Optic Fabry-Perot Interferometry," Proceedings of the SPIE—Second European Workshop on Optical Fibre Sensors, 2004, pp. 304-307, Vol. 5502, No. 1.

Lukosz, W., et al., "Output grating Coulers on Planar Optical Waveguides as Direct Immunosensors", Biosensors & Bioelectronics, vol. 6, 1991, pp. 227-232.

Lundstrom, I., et al. "Immunosensors Based on Surface Plasmon Resonance", The Third World Congress on Biosensors: Abstracts, 1991, p. 91.

Ogert et al., "Detection of Clostridium Botulinum Toxin A Using a Fiber Optic-Based Biosensor", Analytical Biochemistry, vol. 205, 1992, pp. 306-312.

PCT International Search Report and Written Opinion; PCT/US04/36830, Sep. 6, 2005, 9 pages.

PCT International Search Report and Written Opinion, PCT/US06/22964, Jun. 1, 2007, 9 pages.

Rudraraju, S. et al., "Acoustic Wave Propagation in Composite Materials: an Experimental Study", SPIE, vol. 2191, Jul. 1994, pp. 487,493.

Schneider, I. et al., "Herbicide Detection Using Reaction, Centers Integrated Into Liposomes Binding to Grating Couplers", The Third World Congress on Biosensors: Abstracts, 1994, p. 271.

Tiefenthaler, K., "Grating Couplers as Label-free Biochemical Waveguide Sensors", Biosensors & Bioelectronics, vol. 8, No. 7-8, pp. xxxv-xxxvii, 1993.

Weber, A. et al., "Fiber-optic Fluorimetry in Biosensors: Comparison Between Evanescent Wave Generation and Distal-face Generation of Fluorescent Light", Biosensors & Bioelectronics, vol. 7, 1992, pp. 193-197.

Yang Y. et al., "Direct Monitoring of Antigen-Antibody Interactions by Optical Fiber Bioprobe," Proceedings of the SPIE, Jun. 8, 2003, pp. 431-436, vol. 5254, No. 1.

Yang, Y. et al., "Study of Optical Fiber Biosensor Based on White-Light Interferometry," Journal of Xi'An Jiaotong University, Sep. 2003, pp. 914-916, 988, vol. 37, No. 9, Xian, CN.

Supplementary European Search Report for European Patent Application No. EP 06784824, Feb. 23, 2009, 6 pages.

* cited by examiner

FIBER-OPTIC ASSAY APPARATUS BASED ON PHASE-SHIFT INTERFEROMETRY

CROSS REFERENCE TO RELATED APPLICATIONS

This application is a continuation of U.S. patent application Ser. No. 11/423,671, filed Jun. 12, 2006; which (a) is a continuation-in-part of U.S. patent application Ser. No. 10/981,901, filed Nov. 4, 2004; which claims the benefit of U.S. Provisional Application No. 60/518,068, filed Nov. 6, 2003 and of U.S. Provisional Application No. 60/558,381, filed Mar. 31, 2004; and which (b) also claims the benefit of U.S. Provisional Application No. 60/690,324, filed Jun. 13, 2005. The disclosures of all of the foregoing are hereby incorporated by reference in their entirety including any appendices or attachments thereof for all purposes.

STATEMENT REGARDING FEDERALLY SPONSORED RESEARCH OR DEVELOPMENT

Not applicable.

BACKGROUND OF THE INVENTION

1. Field of the Invention

The present invention relates to an apparatus and method for detecting the presence, amount, or rate of binding of one or more analytes in a sample, and in particular, to apparatus and method based on fiber optic interferometry.

2. Description of the Related Art

Diagnostic tests based on a binding event between members of an analyte-anti-analyte binding pair are widely used in medical, veterinary, agricultural and research applications. Typically, such methods are employed to detect the presence or amount or an analyte in a sample, and/or the rate of binding of the analyte to the anti-analyte. Typical analyte-anti-analyte pairs include complementary strands of nucleic acids, antigen-antibody pairs, and receptor-receptor binding agent, where the analyte can be either member of the pair, and the anti-analyte molecule, the opposite member.

Diagnostics methods of this type often employ a solid surface having immobilized anti-analyte molecules to which sample analyte molecules will bind specifically and with high affinity at a defined detection zone. In this type of assay, known as a solid-phase assay, the solid surface is exposed to the sample under conditions that promote analyte binding to immobilized anti-analyte molecules. The binding event can be detected directly, e.g., by a change in the mass, reflectivity, thickness, color or other characteristic indicative of a binding event. Where the analyte is pre-labeled, e.g., with a chromophore, or fluorescent or radiolabel, the binding event is detectable by the presence and/or amount of detectable label at the detection zone. Alternatively, the analyte can be labeled after it is bound at the detection zone, e.g., with a secondary, fluorescent-labeled anti-analyte antibody.

Co-owned U.S. Pat. No. 5,804,453, (the '453 patent) which is incorporated herein by reference, discloses a fiber-optic interferometer assay device designed to detect analyte binding to a fiber-optic end surface. Analyte detection is based on a change in the thickness at the end surface of the optical fiber resulting from the binding of analyte molecules to the surface, with greater amount of analyte producing a greater thickness-related change in the interference signal. The change in interference signal is due to a phase shift between light reflected from the end of the fiber and from the binding layer carried on the fiber end, as illustrated particularly in FIGS. 7a and 7b of the '453 patent.

Ideally, an interferometer assay device will have advantages of simplicity and economy of use, flexibility to detect different types of analytes using the same basic device, and economies of scale. The present invention provides some or all of these advantages.

SUMMARY OF THE INVENTION

The invention includes, in one aspect, an apparatus for detecting an analyte in a sample, including detecting the presence of analyte, the amount of analyte or the rate of association and/or dissociation of analyte to analyte-binding molecules. The apparatus includes a light source, a detector unit and one or more disposable detector tips. The apparatus also includes an optical coupling assembly that couples light from the source to the detector tips and couples reflected light from the detector tips to the detector unit.

The detector tips include two reflecting surfaces separated by at least 50 nm. Light from the source is directed to and reflected from the two reflecting surfaces. The interfering reflected beams are directed to the detector unit. The detector tip also includes a deposit of analyte binding molecules that is positioned so that the interference between the reflected beams varies as analyte binds to the analyte-binding molecules.

In one aspect, the optical coupling assembly includes a source connector assembly for optically coupling to the light source, a detector connector assembly for optically coupling to the detector unit, and a tip connector assembly for optical coupling to the detector tips. The disposable detector tips can be removably attached to the tip connector assembly thus facilitating the rapid replacement of used tips and the use of different types of tips. A source fiber assembly optically couples the source connector assembly to the tip connector assembly, and a detector fiber assembly optically couples the tip connector assembly to the detector connector assembly.

The optical coupling assembly preferably is constructed from standard parts. For example, the connector assemblies preferably are constructed from standard optical fibers and fiber ferrules, such as SMA ferrules. In one design, the tip connector assembly includes multiple ferrules. Each ferrule optically couples to a detector tip and contains optical fiber(s) from both the source fiber assembly and the detector fiber assembly. In a particular design, the source fiber(s) and the detector fiber(s) are each arranged symmetrically about a central axis. For example, there may be one source fiber and multiple detector fibers arranged in a pattern centered about the source fiber.

In another aspect, the disposable detector tip includes an optical fiber section and a connector structure. The optical fiber section has a proximal end and a distal end and the sensing element is formed on (i.e., supported by) the distal end. The proximal end couples optically to the tip connector assembly. The connector structure is fixedly attached to the optical fiber section and may be removably attached to a tip connector. For example, it may be slid onto and off of a ferrule in the tip connector. In this way, the proximal end of the fiber section can be optically coupled to one or more optical fibers contained in the tip connector.

In one particular design, the connector structure includes a central bore in which the optical fiber section is attached. It also includes flexible gripping arms that slide over a ferrule of the tip connector (e.g., an SMA ferrule). The flexible gripping arms maintain enough frictional force on the ferrule to hold the optical fiber section in position relative to the optical fibers in the ferrule. The connector structure maintains an air gap between the proximal end of the fiber section and the face of the optical fibers in the ferrule. The connector structure includes a flat engagement surface that is approximately flush with the proximal end of the fiber section. Contact of the flat engagement surface with the end of the ferrule maintains the air gap between the proximal end of the fiber section and the optical fibers contained in the tip connector.

BRIEF DESCRIPTION OF THE SEVERAL VIEWS OF THE DRAWING

These and other features, aspects, and advantages of the present invention will become better understood with regard to the following description, and accompanying drawings, where.

DETAILED DESCRIPTION OF THE INVENTION

Definitions

Figure 1:
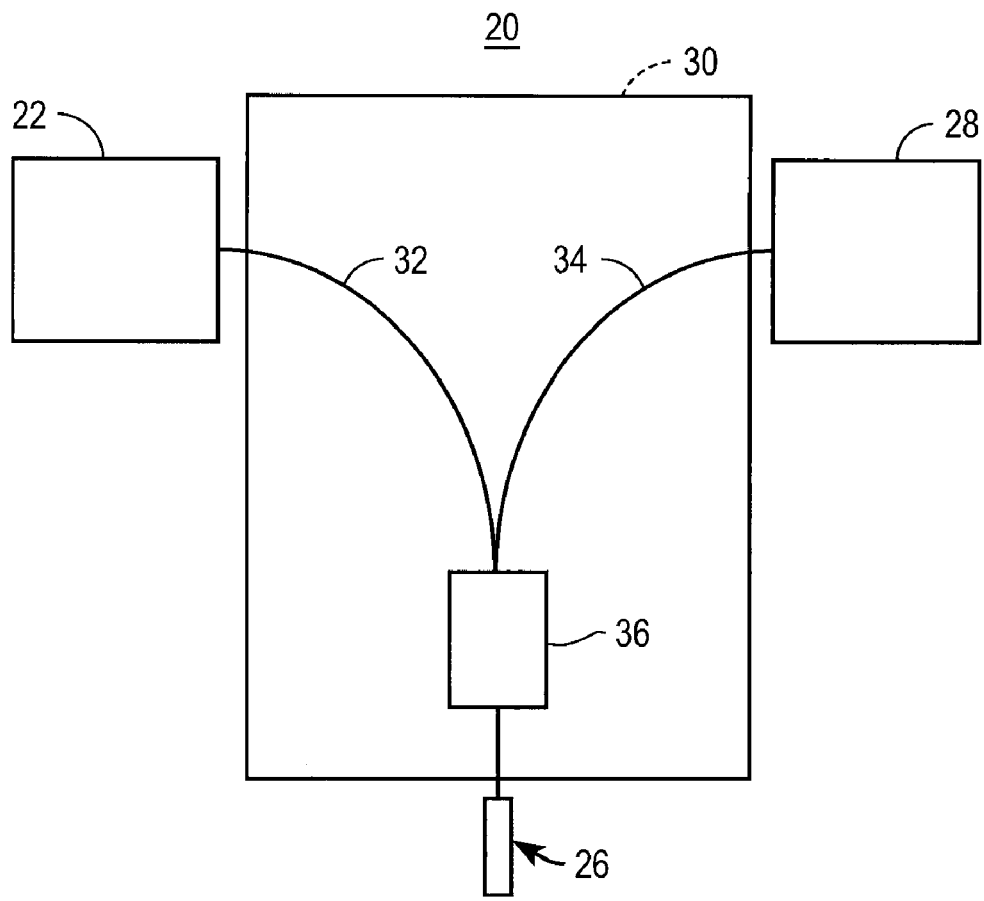
FIG. 1 shows the basic system setup for the bioprobe and its apparatus.

Terms used in the claims and specification are to be construed in accordance with their usual meaning as understood by one skilled in the art except and as defined as set forth below. Numeric ranges recited in the claims and specification are to be construed as including the limits bounding the recited ranges.

The term "in vivo" refers to processes that occur in a living organism.

An "analyte-binding" molecule refers to any molecule capable of participating in a specific binding reaction with an analyte molecule. Examples include but are not limited to, e.g., antibody-antigen binding reactions, and nucleic acid hybridization reactions.

A "specific binding reaction" refers to a binding reaction that is saturable, usually reversible, and that can be competed with an excess of one of the reactants. Specific binding reactions are characterized by complementarity of shape, charge, and other binding determinants as between the participants in the specific binding reaction.

An "antibody" refers to an immunoglobulin molecule having two heavy chains and two light chains prepared by any method known in the art or later developed and includes polyclonal antibodies such as those produced by inoculating a mammal such as a goat, mouse, rabbit, etc. with an immunogen, as well as monoclonal antibodies produced using the well-known Kohler Milstein hybridoma fusion technique. The term includes antibodies produced using genetic engineering methods such as those employing, e.g., SCID mice reconstituted with human immunoglobulin genes, as well as antibodies that have been humanized using art-known resurfacing techniques.

An "antibody fragment" refers to a fragment of an antibody molecule produced by chemical cleavage or genetic engineering techniques, as well as to single chain variable fragments (SCFvs) such as those produced using combinatorial genetic libraries and phage display technologies. Antibody fragments used in accordance with the present invention usually retain the ability to bind their cognate antigen and so include variable sequences and antigen combining sites.

A "small molecule" refers to an organic compound having a molecular weight less than about 500 daltons. Small molecules are useful starting materials for screening to identify drug lead compounds that then can be optimized through traditional medicinal chemistry, structure activity relationship studies to create new drugs. Small molecule drug compounds have the benefit of usually being orally bioavailable. Examples of small molecules include compounds listed in the following databases: MDL/ACD (http://www.mdli.com/), MDL/MDDR (http://www.mdli.com/), SPECS (http://www.specs.net/), the China Natural Product Database (CNPD) (http://www.neotrident.com/), and the compound sample database of the National Center for Drug Screening (http://www.screen.org.cn/).

Abbreviations used in this application include the following: "ss" refers to single-stranded; "SNP" refers to single nucleotide polymorphism; "PBS" refers to phosphate buffered saline (0.01 M phosphate buffer, 0.0027 M potassium chloride and 0.137 M sodium chloride, pH 7.4); "NHS" refers to N-hydroxysuccinimide; "MW" refers to molecular weight; "Sulfo-SMCC" refers to sulfosuccinimidyl 4-[N-maleimidomethyl]cyclohexane-1-carboxylate.

It must be noted that, as used in the specification and the appended claims, the singular forms "a," "an" and "the" include plural referents unless the context clearly dictates otherwise.

Advantages and Utility

The advantages and utility of the invention are illustrated by reference to the Figures and Examples as described in greater detail below. These include the ability to monitor in real time analyte binding reactions without the use of labels, diminishing cost and potential toxicity. A further advantage includes the ability to practice the method using visible wavelength light sources. Yet other advantages are provided by the fiber optic nature of the detector tip that allows binding reactions to be monitored in very small sample volumes, including in "in vitro" spaces, and to bundle fibers to carry out highly multiplexed analyses of binding reactions.

FIG. 1 shows, in schematic view, an interferometer apparatus 20 constructed in accordance with the invention. In its most basic elements, the apparatus includes a light source 22, an optical assembly 26 that functions as a sensing element or detector tip and that will be detailed further with respect to FIGS. 2, 4 and 5 below, and a detector unit 28 for detecting interference signals produced by interfering light waves reflected from the optical assembly 26.

Light from source 22 is directed onto the optical assembly 26, and reflected back to the detector through an optical coupling assembly indicated by dashed lines at 30. In a preferred embodiment, the coupling assembly includes a first fiber assembly 32 (referred to as the source fiber assembly for convenience) that carries light from the light source to the optical assembly 26, and a second fiber assembly 34 (the detector fiber assembly) which carries reflected light from the optical assembly 26 to the detector. Optionally, an optical coupler 36 may be used to optically couple the fiber assemblies 32, 34 to the optical assembly 26.

The light source in the apparatus can be a white light source, such as a light emitting diode (LED) which produces light over a broad spectrum, e.g., 400 nm or less to 700 nm or greater, typically over a spectral range of at least 100 nm. Alternatively, the light source can be a plurality of sources each having a different characteristic wavelength, such as LEDs designed for light emission at different selected wavelengths in the visible light range. The same function can be achieved by a single light source, e.g., white light source, with suitable filters for directing light with different selected wavelengths onto the optical assembly.

The detector is preferably a spectrometer, such as charge-coupled device (CCD), capable of recording the spectrum of the reflected interfering light from the optical assembly. Alternatively, where the light source operates to direct different selected wavelengths onto the optical assembly, the detector can be a simple photodetector for recording light intensity at each of the different irradiating wavelengths. In still another embodiment, the detector can include a plurality of filters which allows detection of light intensity, e.g., from a white-light source, at each of a plurality of selected wavelengths of the interference reflectance wave.

Figure 2:
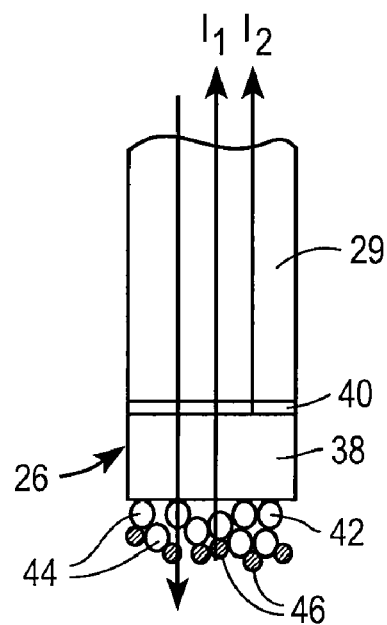
FIG. 2 shows an optical assembly formed accordance to one embodiment of the invention.

FIG. 2 shows the optically functional part of an optical assembly 26 constructed in accordance with one embodiment of the invention. The optical assembly 26 includes a short length of optical fiber 29, on which the remainder of the optical assembly is formed. The other end of optical fiber 29 is optically coupled to the fiber assemblies 32 and 34, respectively. As seen, the assembly 26 includes a transparent optical element 38 having first and second reflecting surfaces 42, 40. According to an important feature of the invention, the thickness "d" of the optical element between the two reflecting surfaces is at least 50 nm, and preferably at least 100 nm. An exemplary thickness is between about 100-5,000 nm, preferably 400-1,000 nm. The first reflecting surface 42 is formed of a layer of analyte-binding molecules, such as molecules 44, which are effective to bind analyte molecules 46 specifically and with high affinity. That is, the analyte and anti-analyte molecules are opposite members of a binding pair of the type described above, which can include, without limitations, antigen-antibody pairs, complementary nucleic acids, and receptor-binding agent pairs.

The index of refraction of the optical element is preferably similar to that of the first reflecting surface, so that reflection from the lower distal end of the optical assembly occurs predominantly from the layer formed by the analyte-binding molecules, rather than from the interface between the optical element and the analyte-binding molecules. Similarly, as analyte molecules bind to the lower layer of the optical assembly, light reflection form the lower end of the assembly occurs predominantly from the layer formed by the analyte-binding molecules and bound analyte, rather than from the interface region. One exemplary material forming the optical element is $SiO_2$, e.g., a high-quality quality glass having an index of refraction of about 1.4-1.5. The optical element can also be formed of a transparent polymer, such as polystyrene or polyethylene, having an index of refraction preferably in the 1.3-1.8 range.

The second reflecting surface in the optical assembly formed as a layer of transparent material having an index of refraction that is substantially higher than that of the optical element, such that this layer functions to reflect a portion of the light directed onto the optical assembly. Preferably, the second layer has a refractive index greater than 1.8. One exemplary material for the second layer is $Ta_2O_5$ with refractive index equal to 2.1. The layer is typically formed on the optical element by a conventional vapor deposition coating or layering process, to a layer thickness of less than 50 nm, typically between 5 and 30 nm.

The thickness of the first (analyte-binding) layer is designed to optimize the overall sensitivity based on specific hardware and optical components. Conventional immobilization chemistries are used in chemically, e.g., covalently, attaching a layer of analyte-binding molecules to the lower surface of the optical element. For example, a variety of bifunctional reagents containing a siloxane group for chemical attachment to $SiO_2$, and an hydroxyl, amine, carboxyl or other reaction group for attachment of biological molecules, such as proteins (e.g., antigens, antibodies), or nucleic acids. It is also well known to etch or otherwise treat glass a glass surface to increase the density of hydroxyl groups by which analyte-binding molecules can be bound. Where the optical element is formed of a polymer, such as polystyrene, a variety of methods are available for exposing available chemically-active surface groups, such as amine, hydroxyl, and carboxyl groups.

The analyte-binding layer is preferably formed under conditions in which the distal surface of the optical element is densely coated, so that binding of analyte molecules to the layer forces a change in the thickness of the layer, rather than filling in the layer. The analyte-binding layer can be either a monolayer or a multi-layer matrix.

The measurement of the presence, concentration, and/or binding rate of analyte to the optical assembly is enabled by the interference of reflected light beams from the two reflecting surfaces in the optical assembly. Specifically, as analyte molecules attach to or detach from the surface, the average thickness of the first reflecting layer changes accordingly. Because the thickness of all other layers remains the same, the interference wave formed by the light waves reflected from the two surfaces is phase shifted in accordance with this thickness change.

Assume that there are two reflected beams: The first beam is reflected from the first surface, which is the distal end interface between analyte-binding molecules and bound analyte and the surrounding medium; and the second beam is reflected from the second surface, which is the proximal interface between the optical element (the first layer) and the high-index of refraction layer (the second layer). The overall wavelength-dependent intensity of the interference wave is:

$$I = I_1 + I_2 + 2\sqrt{I_1 I_2} \cos\left(\frac{2\pi\Delta}{\lambda}\right)$$

where I is the intensity, $I_1$ and $I_2$ are the intensity of two interference beams, $\Delta$ is the optical path difference, and $\lambda$ is the wavelength.

When $(2\pi\Delta/\lambda)=N\pi$, the curve is at its peak or valley if N is an integer 0, 1, 2, . . . . The thickness of the first layer $d=\Delta/2n$. Therefore, $\lambda=4nd/N$ at peaks or valleys (extrema). For the first several values of N. i.e., 0, 1, 2, . . . 7, and assuming a d of 770 nm, the equation gives:

N=0: $\lambda=\infty$ (peak)
N=1: $\lambda=4nd=4,496.80$ nm (Valley)
N=2: $\lambda=2nd=2,248.40$ nm (Peak)
N=3: $\lambda=4nd/3=1,498.9$ nm (Valley)
N=4: $\lambda=nd=1,124.20$ nm (Peak)
N=5: $\lambda=4nd/5=899.36$ nm (Valley)
N=6: $\lambda=2nd/3=749.47$ nm (Peak)
N=7: $\lambda=4nd/7=642$ nm (Valley)
N=8: $\lambda=nd/2=562$ nm (Peak)
N=9: $\lambda=4nd/9=499.64$ nm (Valley)
N=10: $\lambda=4nd/10=449.6$ nm (Peak)

Figure 3A:
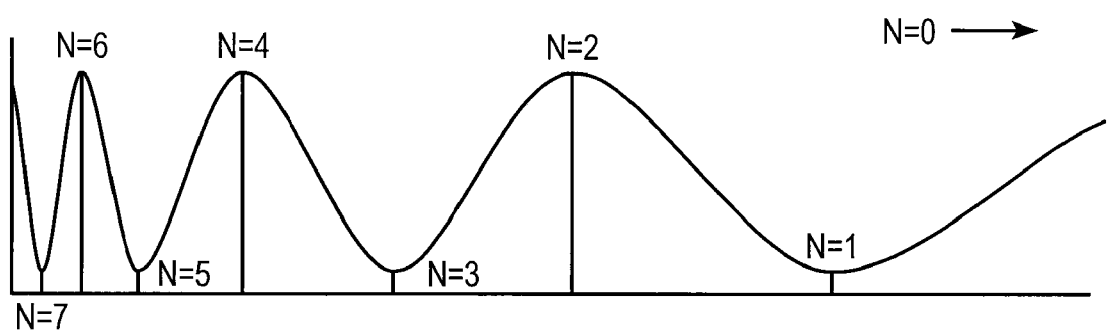
FIGS. 3A and 3B show a portion of an interference wave over 7 peak and valley orders (3A), and over in a visible portion of the spectrum (3B)
Figure 3B:
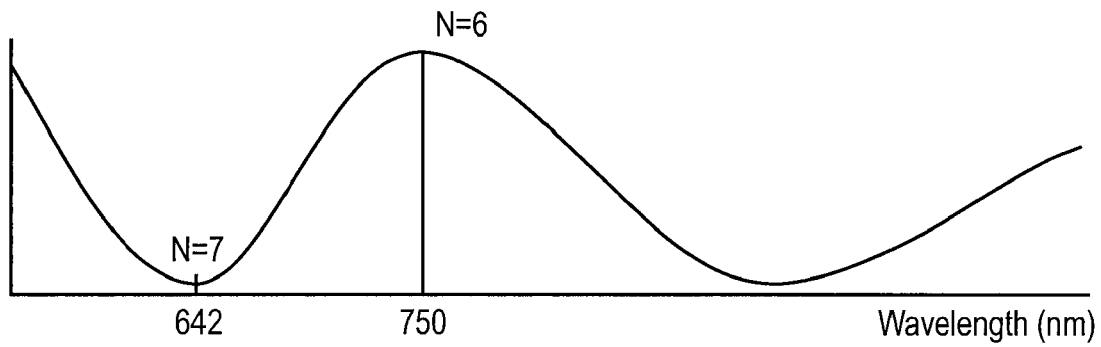

As can be seen, and illustrated further in FIGS. 3A and 3B, at least three peaks/valleys (N=7-9) occur in the visible spectral range.

If the $7^{th}$ order valley is used to calculate the change in molecular layer thickness, when the molecular layer attached to the first layer increases from 0 nm to 10 nm, the $7^{th}$ order valley will shift to 650.74 nm. Therefore, the ratio between the actual the phase shift of the $7^{th}$ order valley and thickness change equals (650.74−642.40)/10=0.834.

By contrast, if the initial spacing between the two reflecting layers is made up entirely of the analyte-binding molecules on the end of the fiber, assuming a thickness of this layer of 25 nm, then the first order peak will occur at 146 nm, clearly out of the range of the visible spectrum, so that the device will only see a portion of the region between the 0-order valley and the first order peak, but will not see any peaks, making a shift in the spectral characteristics of the interference wave difficult to measure accurately.

Not until the total thickness of the reflecting layer approaches about 100 nm will the first-order peak appear in the visible spectrum. Assuming a total thickness change of up to 50 nm, the thickness of the optical element can then be as small as 50 nm, but is preferably on the order of several hundred nm, so that the phase shift or change in periodicity of the interference wave can be measured readily by a shift in the spectral positions of higher-order peaks or valleys, e.g., where N=3-10.

The ratio between the actual thickness and the measured phase shift is considered as a key factor of measurement sensitivity. It can be appreciated how one can adjust the thickness of the optical element and its refractive index to improve and optimize the sensitivity to accommodate the electronics and optical designs.

Figure 4A:
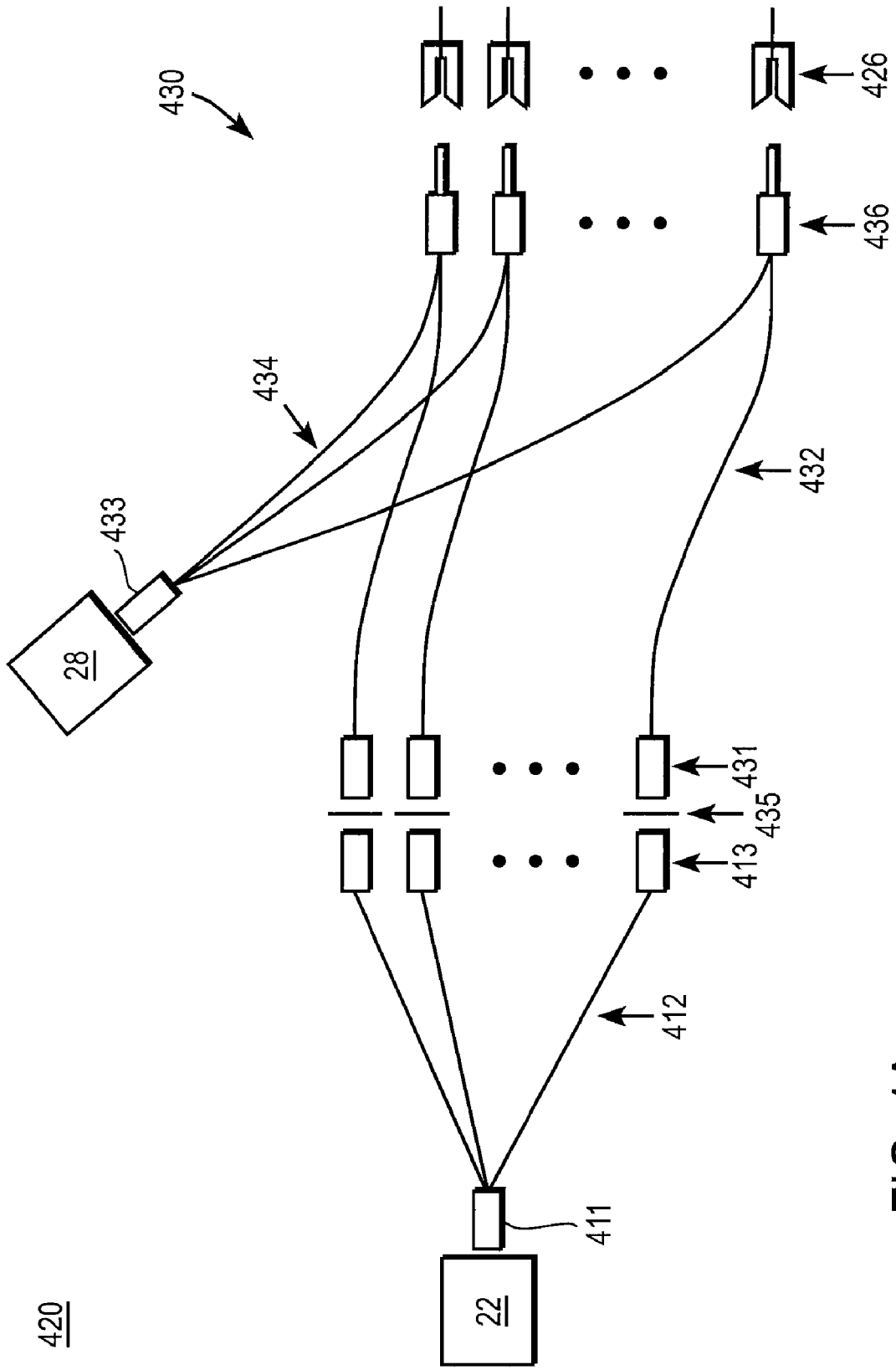
FIG. 4A shows an optical coupling assembly constructed according to the invention.

FIG. 4A shows an example implementation 420 of an assay apparatus 20. In this example, the optical element 26 is implemented as a disposable tip 426 (shown in FIG. 4 as detached from the rest of the apparatus) and the apparatus is designed to use up to eight disposable tips 426 at once. The optical coupling assembly 30 is implemented as a collection 430 of fiber assemblies and connectors. It is removably attachable to the light source 22, the detector tips 426 and the detector unit 28. This modular implementation allows different types of optical coupling assemblies 430 to be used with the same light source 22 and/or detector unit 28, and also allows different types of detector tips 426 to be used with the same optical coupling assembly 430. Corresponding software changes for the detector unit 28 may be made to accommodate these changes.

In this example, working from the light source 20 to the detector unit 28, 56 fibers 412 are coupled to the light source 22 via a standard SMA fiber connector 411. The 56 fibers are arranged as eight bundles of seven fibers each. Each of the bundles terminates in a fiber connector 413, which is optically coupled to another fiber connector 431. For convenience, fiber connectors 431 will be referred to as the source connectors 431 (or collectively as the source connector assembly) since they optically couple the source 20 to the detector tips 426. The fiber bundle running from each source connector 431 to the corresponding detector tip contains a single fiber. Thus, each fiber connection 413-431 couples seven fibers in connector 413 to a single fiber in connector 431. The overall connection couples 56 fibers in the connector assembly 413 to eight fibers in the source connector assembly 431. Shutters 435 are located between the two connector assemblies 413-431.

Seven fibers are used in the bundle for each connector 413 in order to improve the homogeneity of the light provided by source 22. Using seven fibers per bundle results in a total of 56 fibers receiving light from source 22. These 56 fibers can be arranged in a manner that results in more uniform light coupled into each of the single fibers of source connectors 431. The shutters 435 are used to gate which of the detector tips 426 is illuminated at any one time, as will be further described below.

In the optical coupling assembly 430, the source connectors 431 are coupled by a fiber assembly 432 (referred to as the source fiber assembly) to connectors 436 (referred to as the tip connectors or, collectively, as the tip connector assembly), that then couple to the disposable detector tips 426. The source fiber assembly 432 includes eight bundles of one fiber each. The one fiber from each bundle terminates in a separate tip connector 436. The tip connectors 436 also contain fiber bundles 434 destined for the detector unit 28. In this example, the fiber assembly 434 between the tip connectors 436 and the connector(s) to the detector unit (the detector connector assembly 433) contains eight bundles of seven fibers each. Thus, each tip connector 436 contains one fiber from the source fiber assembly 432 and seven fibers from the detector fiber assembly 434.

Figure 4B:
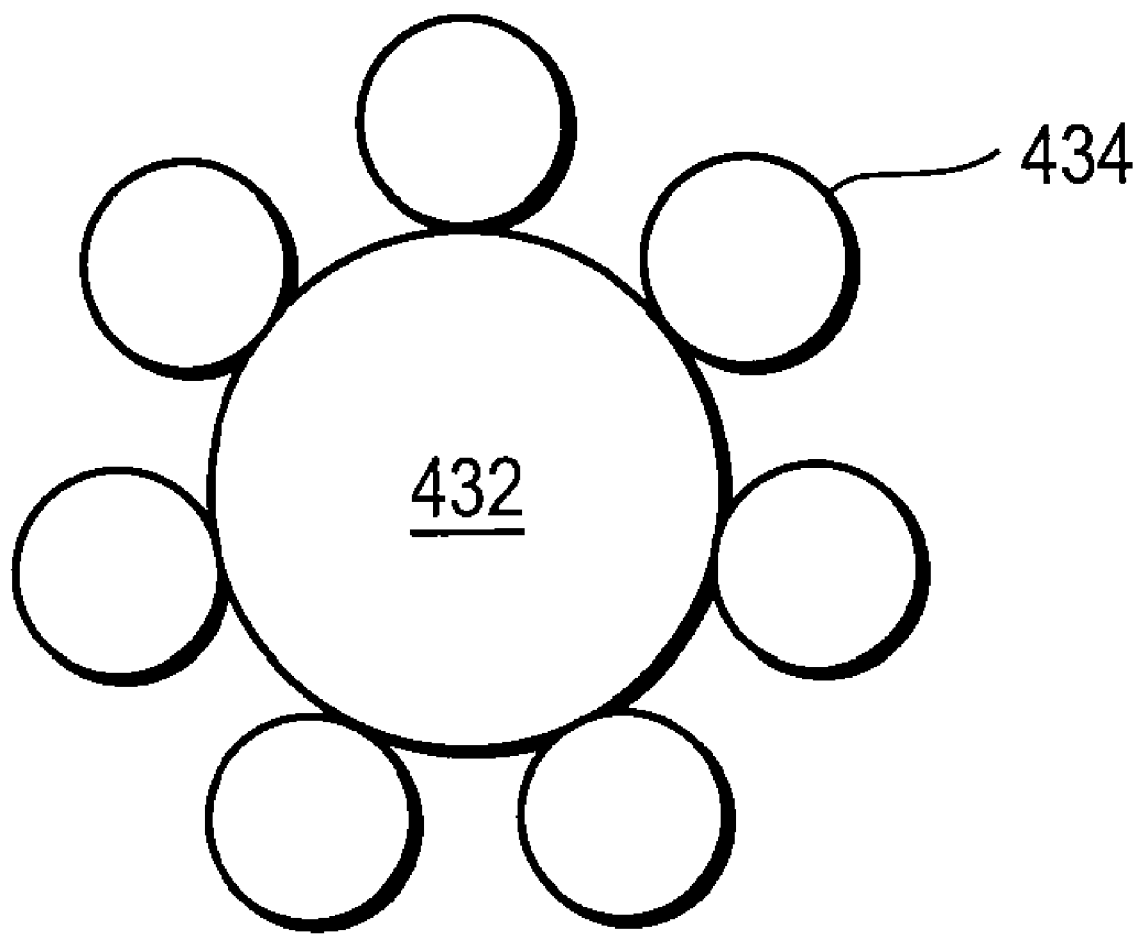
FIG. 4B shows the arrangement of fibers in the tip connector of the optical coupling assembly of FIG. 4A.

These fibers are arranged as shown in FIG. 4B. The detector fibers 434 are arranged in a pattern centered about the source fiber 432. This pattern is used to reduce sensitivity to misalignment between the fibers 432, 434 and the fiber section 29 in the detector tip 26 (see FIG. 2). Light from the source fiber 432 is coupled into the fiber section 29 in the detector tip, where it propagates to the interference structure and is reflected back to be collected by the detector fibers 434. As will be described in FIG. 5, the optical coupling in this example is a direct fiber-to-fiber coupling across a small air gap. Lateral misalignment of fibers could result in reduced coupling but the symmetric arrangement of fibers reduces the sensitivity to lateral misalignment.

Returning to FIG. 4A, the eight fiber bundles 434 from the tip connectors 436 terminate in a single detector connector 433, which optically couples into the detector unit 28 allowing for analysis of the interference signal.

In optical coupling assembly 430, the connectors 411, 413, 431, 436 and 433 are preferably based on standard connectors, typically SMA connectors. Even if the entire connector structure is not used, the connectors preferably will use at least a standard ferrule (e.g., an SMA ferrule) for terminating the relevant fiber bundle. The fibers used in optical coupling assembly 430 are all multimode fibers in this example.

Figure 5A:
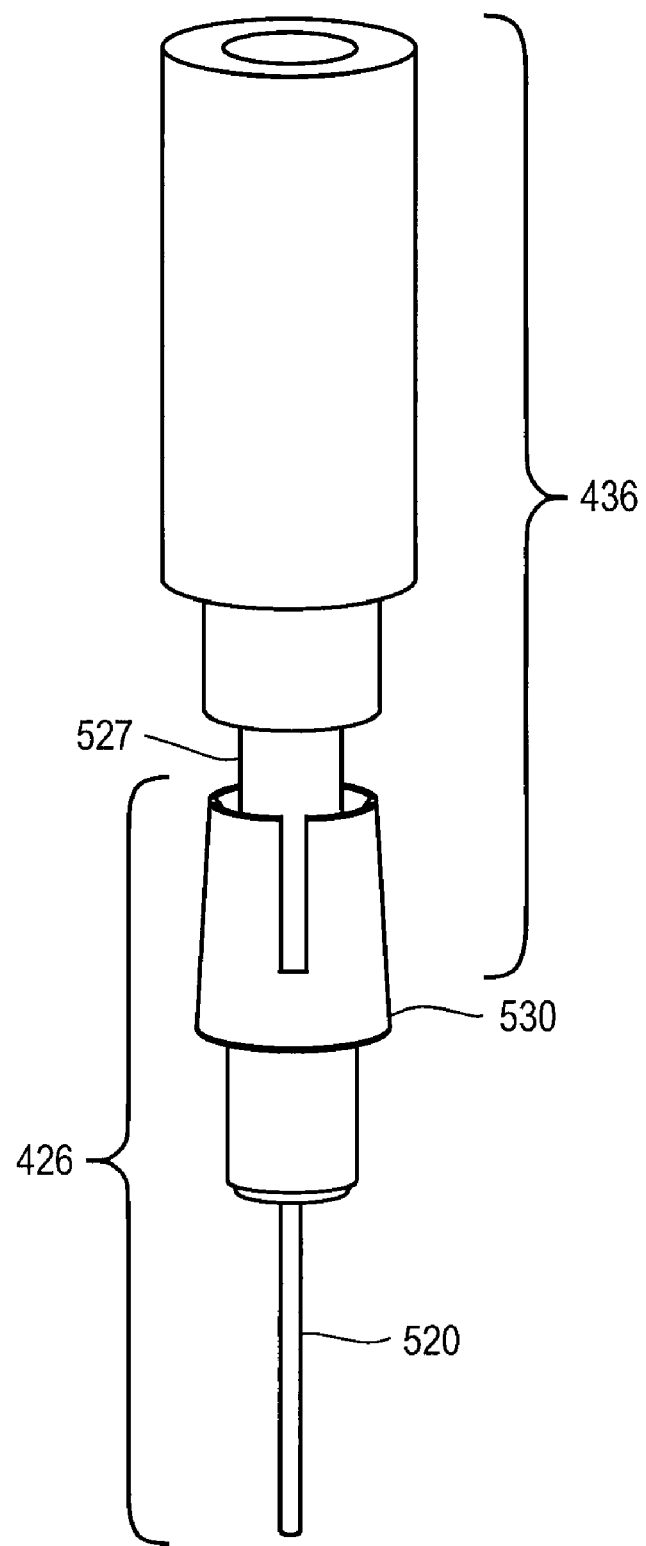
FIG. 5A is a perspective view of the tip connector and detector tip of FIG. 4.
Figure 5B:
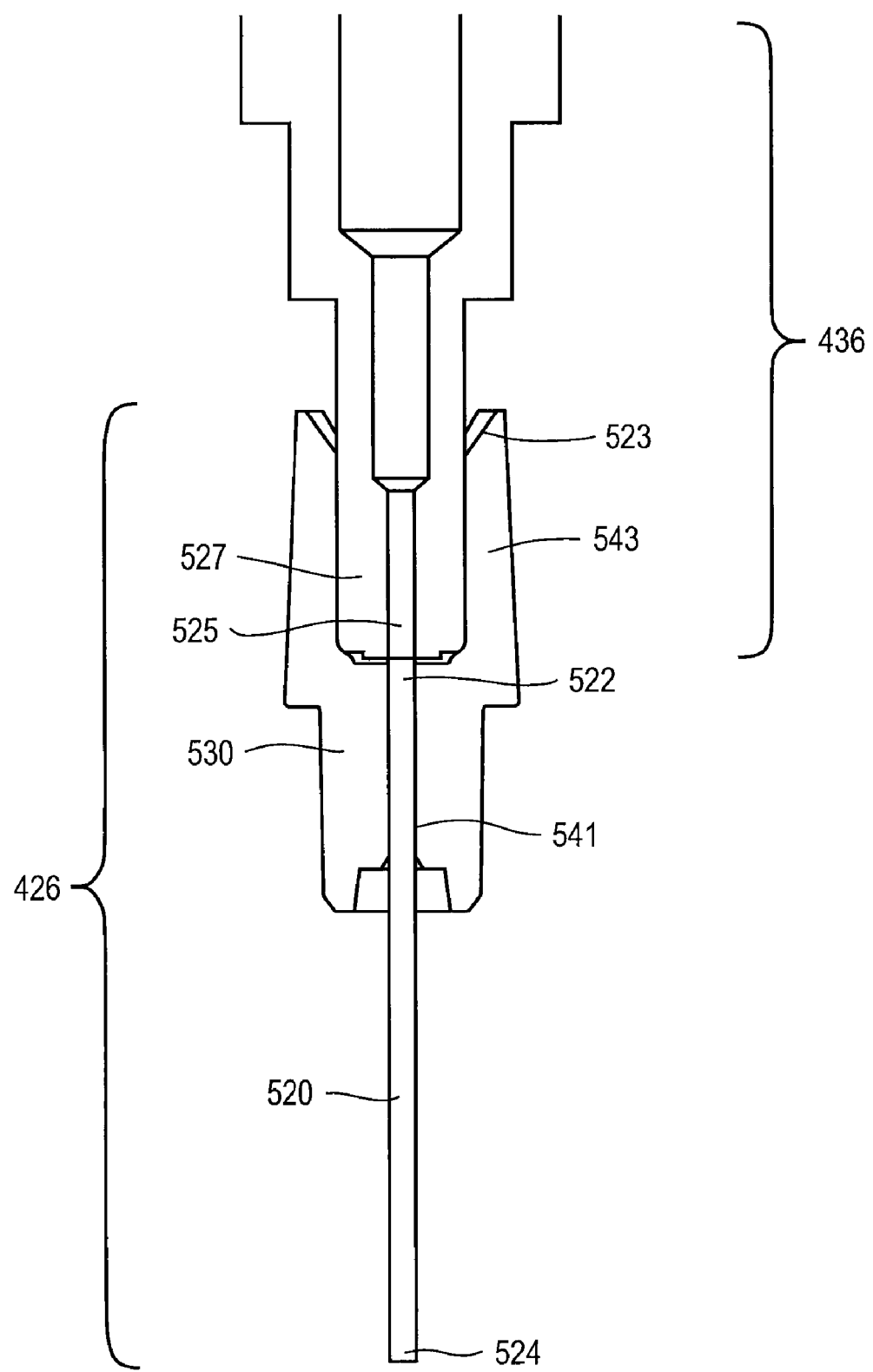
FIG. 5B is a cross-sectional view of the tip connector inserted into the detector tip.
Figure 5C:
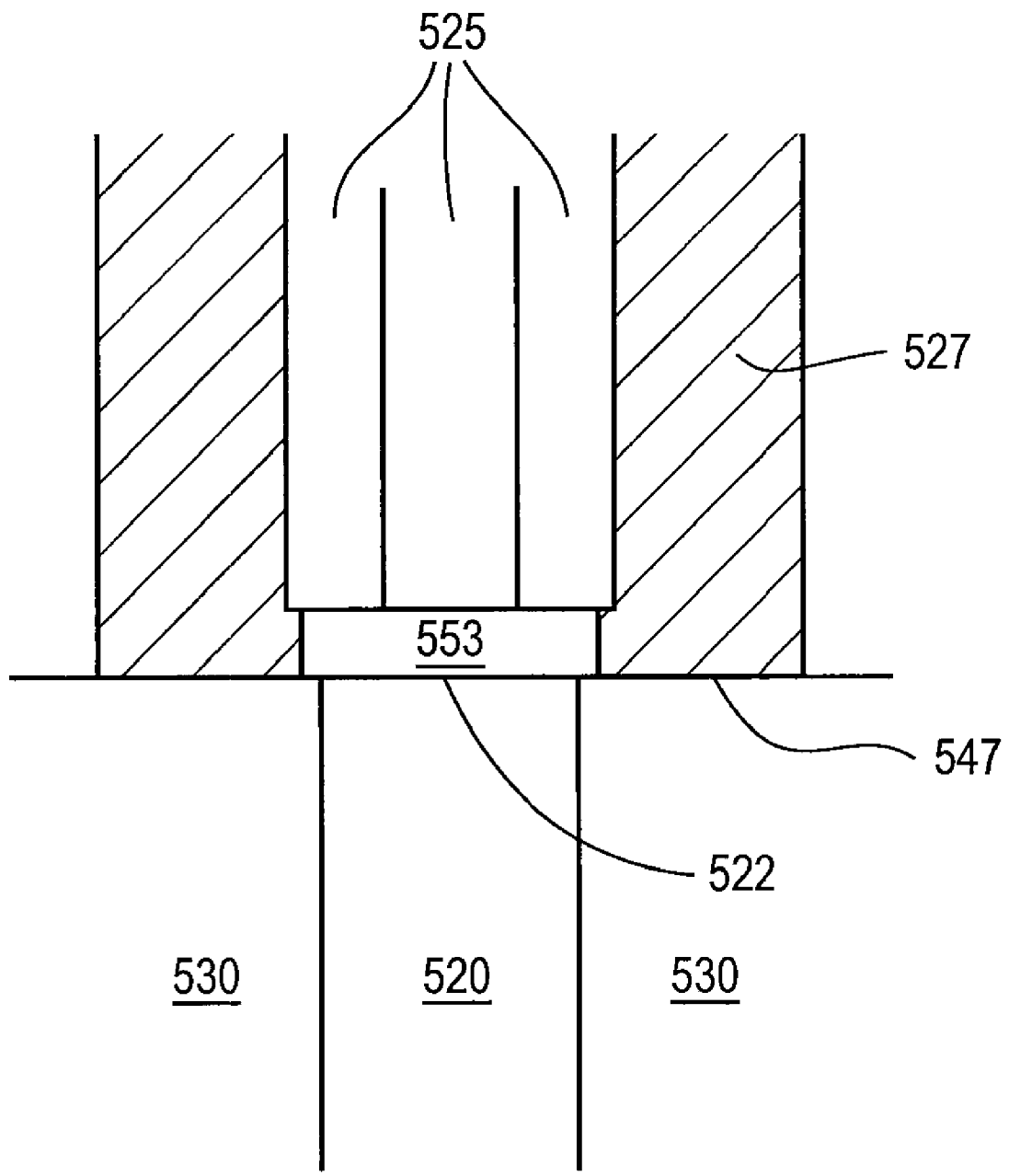
FIG. 5C is a detailed view of the optical coupling between the tip connector and the detector tip.

FIGS. 5A-5C show further details of the tip connector 436 and disposable detector tip 426. FIG. 5A is a perspective view showing the tip connector 436 inserted into the detector tip 426. FIG. 5B is a cross-sectional view of the tip connector 436 inserted into the detector tip 426. FIG. 5C is a detailed view of the optical coupling between tip connector 436 and detector tip 426.

Referring first to FIG. 5B, the disposable detector tip 426 includes an optical fiber section 520 and a connector structure 530. The fiber section 520 has a proximal end 522 and a distal end 524. The proximal end 522 optically couples to the fibers in the tip connector 436. The sensing structure is formed on the distal end 524. The sensing structure (not shown in detail in FIG. 5) typically includes two reflecting surfaces that are positioned so that light coupled into the proximal end 522 of the fiber section is reflected in a manner that results in an interference signal. The sensing structure further includes a deposit of analyte binding molecules. Binding of analyte molecules to the deposit causes a change in the interference signal. An example sensing structure is shown in FIG. 2.

The change in interference can be caused by different physical phenomenon. For example, analyte binding can cause a change in the optical path length or in the physical distance between the two reflecting surfaces. Alternately, analyte binding can cause a change in the index or in the optical absorption of material located between the reflecting surfaces. Analyte binding can also cause the layer of analyte binding molecules to swell, resulting in a change in the interference.

The connector structure 530 both holds the fiber section 520 and allows removable attachment to the tip connector 436. In this particular case the fibers 525 in the tip connector 436 are held in a ferrule 527 (specifically, an SMA ferrule). The connector structure 530 is designed so that the ferrule 527 can be slid into the connector structure 530 and then will be held in place by friction, to allow optical coupling between the fiber section 520 and the fibers 525 in the ferrule 527. The connector structure 530 preferably is designed so that it can be attached and detached from the ferrule 527 by hand.

The connector structure shown in FIG. 5B includes a central bore 541 in which the optical fiber section 520 is fixedly attached. The connector structure also includes flexible gripping arms 543 that slide over the ferrule 527 and maintain enough frictional force on the ferrule to hold the optical fiber section 520 in place relative to the optical fibers 525 in the ferrule 527. The edge 523 of the flexible gripping arms that engages the ferrule is beveled to facilitate insertion of the ferrule into the connector structure.

In this particular design, a détente is not used. Rather, the proper axial spacing is achieved by the design of the ferrule 527 and the connector structure 530. As shown in the detail of FIG. 5C, the connector structure 530 includes a flat engagement surface 547 that is approximately flush with the proximal face 522 of the fiber section 520 with a tolerance less than +/−1 mm. When inserted, the ferrule 527 contacts the engagement surface 547. The fibers are positioned in the ferrule and the connector structure 530 so that the fibers have the correct axial positioning when the contact is made.

In particular, an air gap 553 is maintained between the fiber section 520 and the fibers 525 in the ferrule. The air gap reduces sensitivity to lateral misalignment (compared to a situation where the fibers are directly butt coupled to each other) and the concentric arrangement of fibers in the ferrule (see FIG. 4B) further reduces sensitivity to lateral misalignment. The air gap also reduces unwanted reflections and interferences from the two fiber-air interfaces. The air gap preferably is either less than 100 nm or between 2 μm and 5 mm.

In this particular implementation, the connector structure 530 is a single, monolithic structure. Thus, the detector tip 426 only has two pieces (other than the binding chemistry on the tip): the fiber section 520 and the monolithic connector structure 530. Furthermore, the fiber section 520 is sufficiently short and is sufficiently supported by the connector structure 530 that the unsupported portion, which contains the sensing structure, is stiff. This facilitates automated operation since the location of the sensing structure can be more easily predicted.

The apparatus of FIGS. 4 and 5 may be operated in an automated fashion as follows. Due to the design of the detector tip connectors 436 and the detector tips 426, a robotic device can be programmed to insert the tip connectors 436 into the detector tips 426. The detector tips 426 are then immersed in the solution to be analyzed. Different tips can be attached to each tip connector, and each tip can be immersed in a different solution. The shutters 435 operate to illuminate the detector tips 426 one at a time. If the eight channels are labeled A-H, at time t1, shutter 435A may be open while shutters 435B-H are closed. This provides illumination for detector tip 426A, which produces an interference signal that is analyzed by detector unit 28. At time t2, shutter 435A may close and shutter 435B may open, thus providing illumination to detector tip 426B, and so on. Other types of multiplexers can be used. The sequence of illumination can be programmed and preferably is synchronized with analysis performed by the detector unit 428. The robotic device can then replace the used tips with fresh tips, repeating the cycle for further analysis. Other implementations can use different numbers of detector tips, for example 96 to match currently available arrays.

The apparatus described in this invention can be used more specifically for the following applications:

(i) with an anti-species antibody carried on the tip, for screening hybridoma expression lines for cell lines with high antibody expression;

(ii) with an antigen carried on the tip, to characterize high affinity antibodies against that antigen;

(iii) with a protein carried on the tip, for identifying and characterizing binding partners (DNA, RNA, proteins, carbohydrates, organic molecules) for that protein;

(iv) with a carbohydrate or glycosyl moiety carried on the tip, for identifying and characterizing binding partners (such as, e.g., DNA, RNA, proteins, carbohydrates, organic molecules) for that carbohydrate;

(v) with a protein thought to participate in a multi-protein complex carried on the tip, for characterizing the binding components and/or kinetics of complex formation;

(vi) with a small protein-binding molecule carried on the tip, for identifying and characterizing protein binders for that molecule;

(vii) with an antibody carried on the tip, for constructing a calibration curve for the analyte using a set of analytes standards. Using this calibration curve, one can then determine the concentration of the analyte in unknown solutions (cell culture supernatants, biological samples, process mixtures, etc).

(viii) with a single-stranded nucleic acid, e.g., ssDNA or RNA carried on the tip, for identifying and molecules that bind specifically to the nucleic acid.

Using a temperature control block, the apparatus and method can also be used to monitor the binding and characterize the binding of an immobilized ssDNA to an oligonucleotide in solution to perform SNP analysis.

The following examples illustrate various methods and applications of the invention, but are in no way intended to limit its scope.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg *Advanced Organic Chemistry* $3^{rd}$ *Ed.* (Plenum Press) Vols A and B (1992).

Example 1

Small Molecule-protein Binding Reaction

This example demonstrates the capability to detect the binding of protein to small molecule immobilized on a sensor tip and subsequent bindings of multiple antibodies. The two-layer configuration on the tip of an optic fiber is used for this test. The thickness of the first $Ta_2O_5$ layer is 25 nm and the thickness of the second $SiO_2$ layer is 770 nm. The fiber was purchased from Ocean Optics (Dunedin, Fla.). It was manually cut into segments that are 40 mm long. Both ends of these segments were polished to standard mirror surface quality. The polishing method used here was exactly the same as those for optical lenses and mirrors. One surface of these fiber segments was outsourced to an optical coating house for $Ta_2O_5$ layer and $SiO_2$ layer. This vendor employed an ion-beam assisted physical vapor deposition (IAPVD) coater made by Leybold. IAPVD is a commonly used coating technique for anti-reflection and optical filters. The experimental steps included the following (all steps are performed at room temperature unless otherwise noted):

The fiber tip was coated with a polymer monolayer derivatized with biotin. The polymer monolayer was prepared using a biotinylated lipid (custom). This lipid was using to form a lipid monolayer on the surface of water solution. The monolayer was cross linked using UV light for 15 minutes. Clean, dry fibers were then brought in contact with the floating thin film and the biotin polymer was adsorbed onto the fiber tip. The fibers were then dryed at 60° C. for 1 hour. The fiber were then stored under ambient conditions The biosensor tip was immersed in 50 µg/ml streptavidin streptavidin (Pierce Biotechnology, Rockford Ill., cat # 21122) in PBS (Invitrogen, Carlsbad, Calif.; cat # 14190078) for 9 minutes and then rinsed briefly with PBS.

The same tip was dipped into 10 µg/ml rabbit-anti-streptavidin solution (AbCam, Cambridge, Mass.; cat # ab6676-1000) in PBS for 36 minutes and then washed with PBS briefly.

Finally, the tip was immersed in 50 µg/mL donkey-anti-rabbit antibody solution antibody (Jackson ImmunoResearch, West Grove, Pa.; cat# 711-005-152) in PBS for 25 minutes. A final 10 minute rinse was performed in PBS solution.

Figure 6:
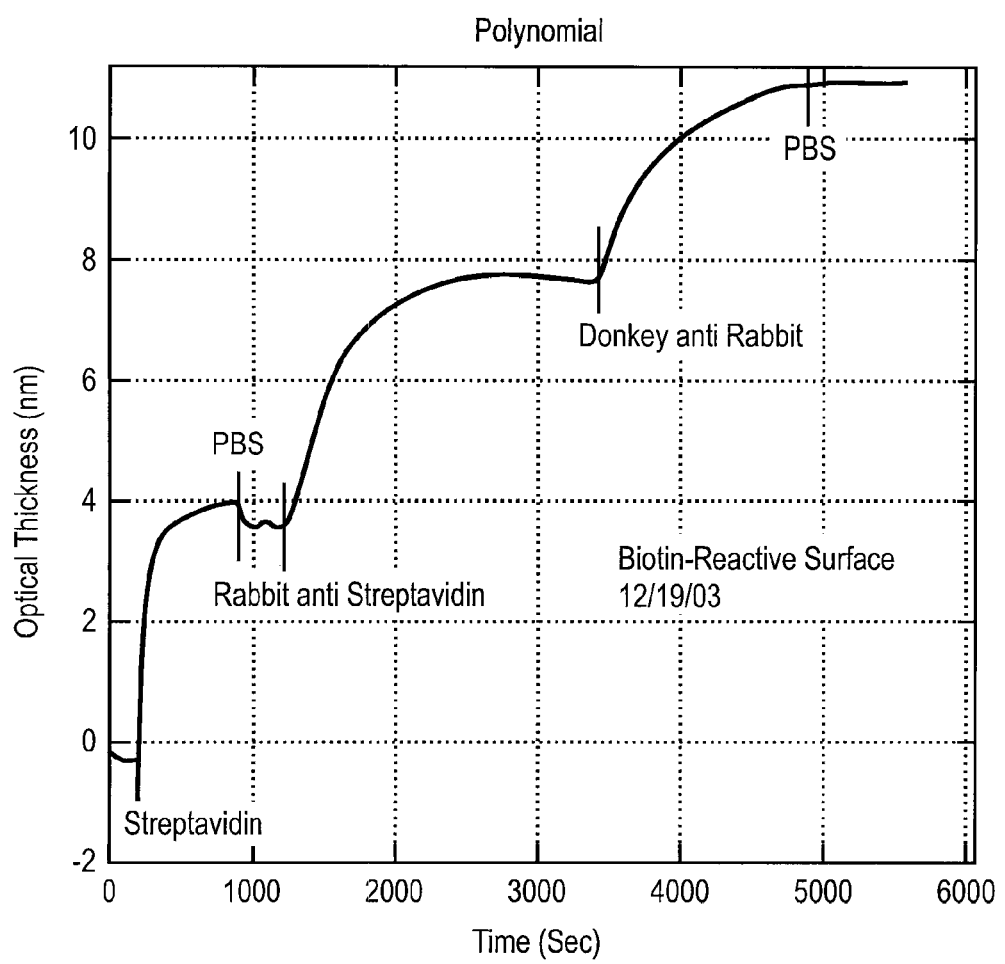
FIG. 6 shows a sequential binding of three molecules.

FIG. 6 shows the real-time response curve for this sequential binding test. The vertical axis is the $7^{th}$ order valley phase shift in nanometers. It clearly shows the binding of streptavidin to the biotin already immobilized on the tip, and subsequent bindings of anti-streptavidin antibody to streptavidin and a second antibody to this first antibody. The dissociation of the streptavidin layer from the tip was visible (a small reduction in the optical thickness) at 900 seconds.

Example 2

Biomolecular Interaction Analysis of Kinetics and Affinity of Biomolecular Interactions This example illustrates use of the invention to carry out a biomolecular interaction analysis (BIA) measuring kinetics and affinity of biomolecular interactions. The same tip configuration as described in Example 1 was used. The experimental steps included the following (all steps are performed at room temperature unless otherwise noted):

Mercaptosilane coated tips were prepared using the following procedure. Clean, dry fibers were incubated in a mixture of Toluene: hexanoic acid: mercaptopropyltrioxysilane (10:2:1 volumetric ratio) at room temperature for 24 hours. The fibers were rinsed 2× with 10 mL toluene for 5 minutes each. The fibers were then rinsed 1× with 10 mL of ethanol and dried under a stream of argon and stored at ambient conditions.

The biosensor tip was first derivatized by immersion in a with 10 µg/ml solution of rabbit-IgG (Jackson ImmunoResearch, West Grove, Pa.; cat# 309-005-003) in PBS for 1 hour.

The coated tip was dipped into 10 µg/ml goat-anti-rabbit antibody solution (Jackson ImmunoResearch, West Grove, Pa.; cat# 111-005-003) in PBS and remained in it for 15 minutes.

The tip was removed and washed in PBS. To facilitate the dissociation of the second antibody from the first antibody, the PBS was agitated manually for 20 minutes.

The tip was then dipped into the same goat-anti-rabbit solution again to show the reproducible association of goat-anti-rabbit to rabbit-IgG.

Figure 7:
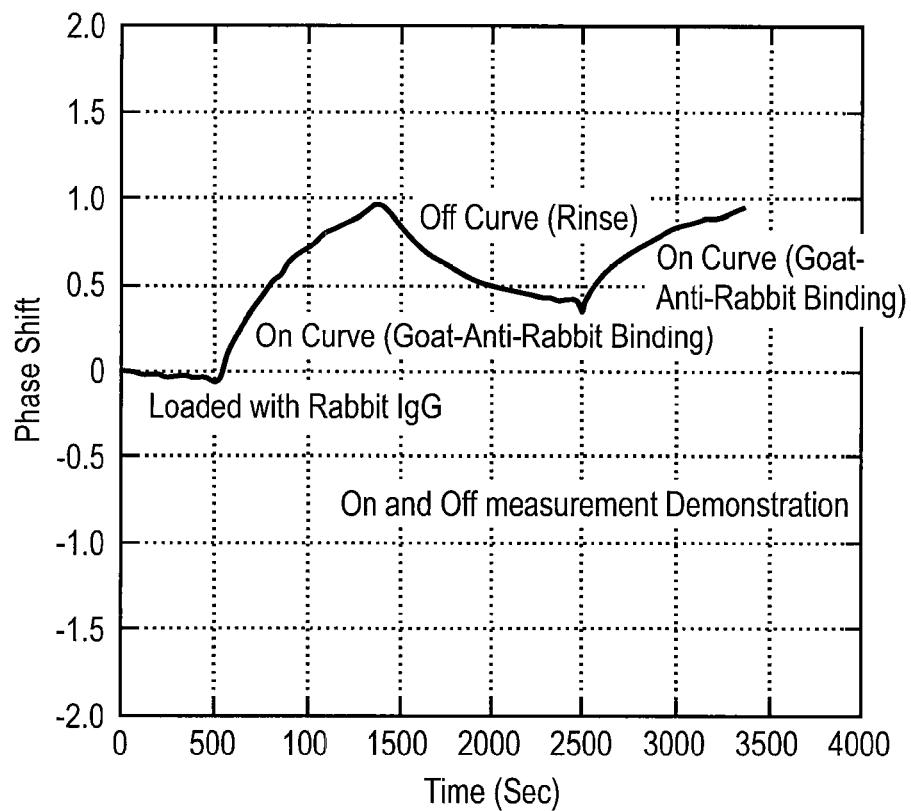
FIG. 7 shows on and off curves generated from the association and dissociation of antibodies.

FIG. 7 shows the on and off curves generated from the association and dissociation of rabbit-IgG and goat-anti-rabbit. The vertical axis is again the $7^{th}$ order valley phase shift. The phase shift is directly related to the average thickness with a ratio of 0.834. The ability to detect the on and off curves reliably is essential for measuring interaction kinetics and affinity.

Example 3

Calculating Affinity Constants from Antibody-antigen Binding and Release Curves This experiment demonstrates the calculation of affinity constants from measuring on and off curves for two antibodies and their antigen. The proprietary antibodies were labeled as Ab-1 and Ab-2. The molecular weight of the antigen was about 30 kilodaltons. The same tip configuration as described in Example 1 was used. The same mercaptosilane fiber preparation as described in Example 2 was used. The experimental steps included (all steps are performed at room temperature unless otherwise noted):

The fiber tip was activated for covalent attachment of the antigen. Mercaptosilane coated fibers were activated by immersing the sensor tips in 50 µL of a 50 mg/mL solution of sulfo-SMCC (Pierce Biotechnology, Rockford Ill.; cat # 22322) in DMF (Sigma-Aldrich Chemical Company, St Louis, Mo.; cat # 494488) at for 2 hours. The sensor tips were rinsed briefly in DMF and dried;

The antigen was covalently bound to the activated fiber tip by immersing the activated tip in a 20 µg/ml solution of antigen in PBS for 20 minutes. The tip was rinsed with PBS for 2 minutes. Following the PBS rinse, the tip was quenched with an aqueous solution of 100 µM ethanolamine pH 8.5 (Sigma-Aldrich Chemical Company, St Louis, Mo.; cat # E9508) for 5 minutes and then was rinsed again in PBS for 2 minutes.

The same tip was immersed in antibody for an association test and the real-time binding data were recorded for 9-15 minutes (depending on the antibody identity and concentration). Once those data were recorded, the tip was again immersed in PBS and agitated to measure the off curve (i.e., dissociation between the immobilized antigen and bound antibody) for 9-15 minutes. The binding (on curve) and dissociation (off curve) measurements were repeated using different concentrations of antibody (25 nM, 150 nM, and 430 nM) and with two different antibodies identified as Ab-1 and Ab-2.

Figure 8:
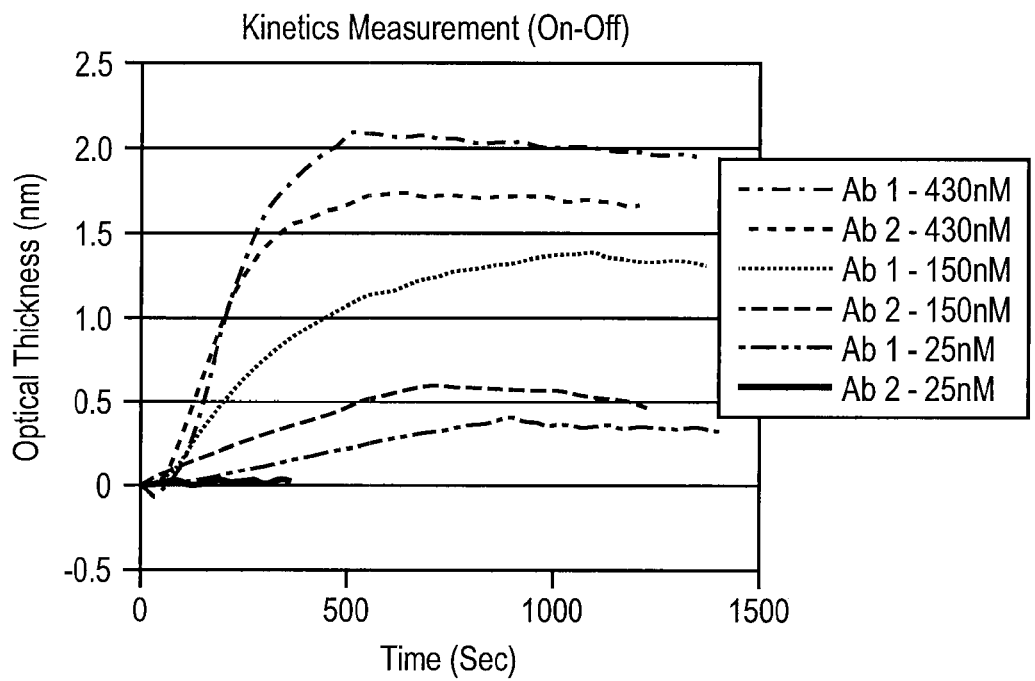
FIG. 8 shows the curves of two antibodies binding to their antigen at different concentrations.

FIG. 8 shows the association and dissociation curves at different concentrations. The test of 25 nM Ab-2 was not completed because the association was extremely slow at this concentration. These illustrated curves are plots of the raw data.

$K_{on}$, $K_{off}$, and $K_D$ were derived from these curves by fitting the raw data with a first order exponential function. By averaging two sets of data, kinetic and affinity coefficients were obtained as follows:

| Ab-1 | Ab-2 |
|---|---|
| $K_{on} = 1.35 \times 10^5$ (M$^{-1}$S$^{-1}$) | $K_{on} = 2.01 \times 10^5$ (M$^{-1}$S$^{-1}$) |
| $K_{off} = 5.55 \times 10^{-5}$ (S$^{-1}$) | $K_{off} = 8.15 \times 10^{-5}$ (S$^{-1}$) |
| $K_D = K_{off}/K_{on} = 3.99 \times 10^{-9}$ (M) | $K_D = K_{off}/K_{on} = 4.45 \times 10^{-9}$ (M) |

Example 4

NHS-ester Activated Tips

The same tip configuration as described in Example 1 was used. The same mercaptosilane fiber preparation as described in Example 2 was used. Mercaptosilane coated fibers were activated by immersing the sensor tips in 50 µL of a 50 mg/nL solution of sulfo-SMCC (Pierce Biotechnology, Rockford Ill.; cat # 22322) in DMF (Sigma-Aldrich Chemical Company, St Louis, Mo.; cat # 494488) at for 2 hours. The sensor tips were rinsed briefly in DMF and dried.

Amine containing molecules can be covalently bound to this surface through formation of a stable amide linkage. Molecules that do not contain free amines are not immobilized through the NHS moiety, but these molecules can still bind to the surface through non-specific binding. This non-specific binding can be multi-layered whereas the covalent immobilization through the NHS esters will be in a single layer controlled by the availability and accessibility of the NHS ester.

In this set of experiments, a bis amino PEG (MW 3300) (Shearwater Polymers, San Carlos, Calif.) was used as a test compound to covalently bind to the activated surface. A PEG (MW 8000) (Sigma-Aldrich Chemical Company, St Louis, Mo.; cat # 04162) that contained no free amino groups was used as a negative control. This negative control was used to look for any non-specific or multi-layered binding that might be inherent to PEG polymers on this surface.

Figure 9:
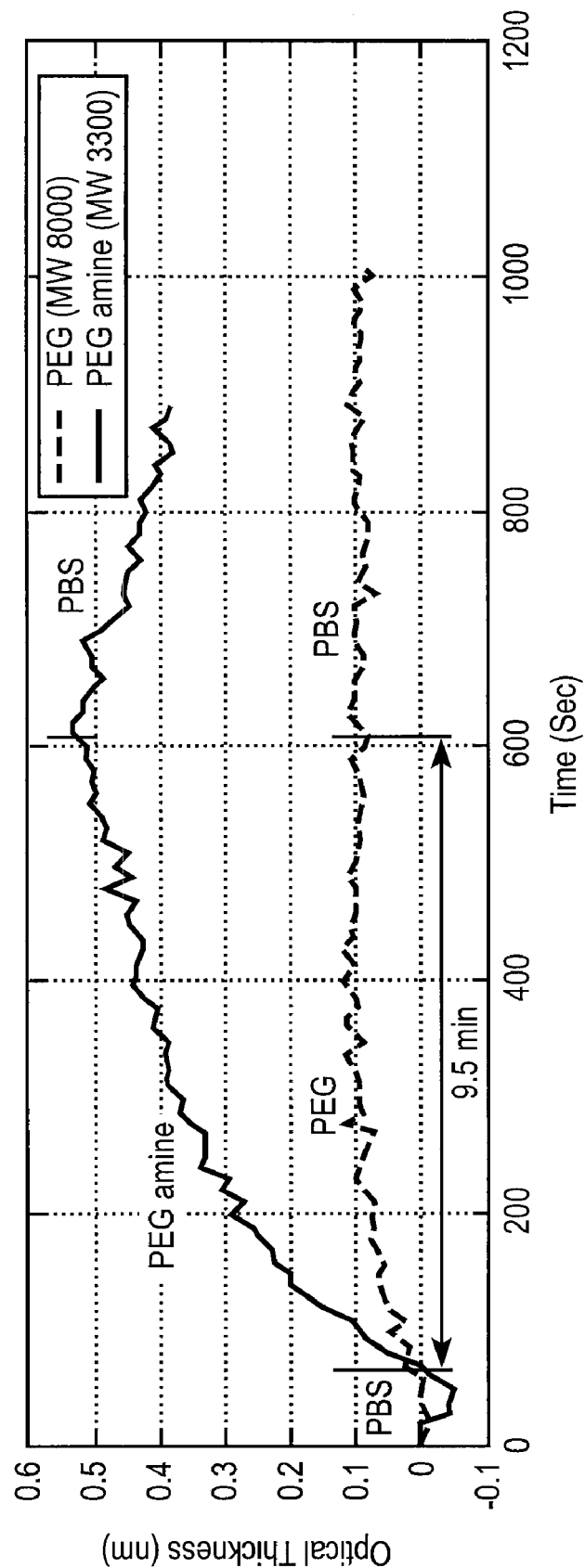
FIG. 9 shows immobilization of bis amino PEG (MW 3300) specifically through an amide bond formation. The PEG (MW 8000) is used as a negative control to monitor non-specific binding of the PEG polymer.

FIG. 9 shows the time course of the treatment of the activated mercaptosilane tip with the test molecules. The activated tip showed a distinct increase in optical thickness upon exposure to the 0.1 mg/mL bis amino PEG (MW 3300) in PBS. This increase is stopped when the bis amino PEG solution is replaced by the PBS buffer. The activated tip exposed to 0.1 mg/mL PEG (MW8000) in PBS, which contains no amines, shows a small initial increase in optical thickness but the trace quickly becomes flat. From this it can be concluded that the PEG polymer does not have intrinsic non-specific binding and that the binding seen for the bis amino PEG is attributed to the specific covalent immobilization of the amine group.

Example 5

Antibody Derivatized Tips Using NHS-ester Chemistry

This example illustrates the binding of a low molecular weight molecule binding to an immobilized high molecular weight molecule. Using the same NHS ester terminated surface described in Example 4 and the same tip configuration as described in Example 1, an anti-biotin antibody was immobilized to 3 fibers. Immobilization of the antibody was accomplished by immersing the activated fiber in a 20 µg/mL solution of mouse anti-biotin antibody (Biodesign, Saco Minn.; cat #H61504M) in PBS for 1 hour at room temperature. The tip was rinsed with PBS for 2 minutes. Following the PBS rinse, the tip was quenched with an aqueous solution of 100 µM ethanolamine pH 8.5 (Sigma-Aldrich Chemical Company, St Louis, Mo.; cat # E9508) for 5 minutes and then was rinsed again in PBS for 2 minutes.

Figure 10:
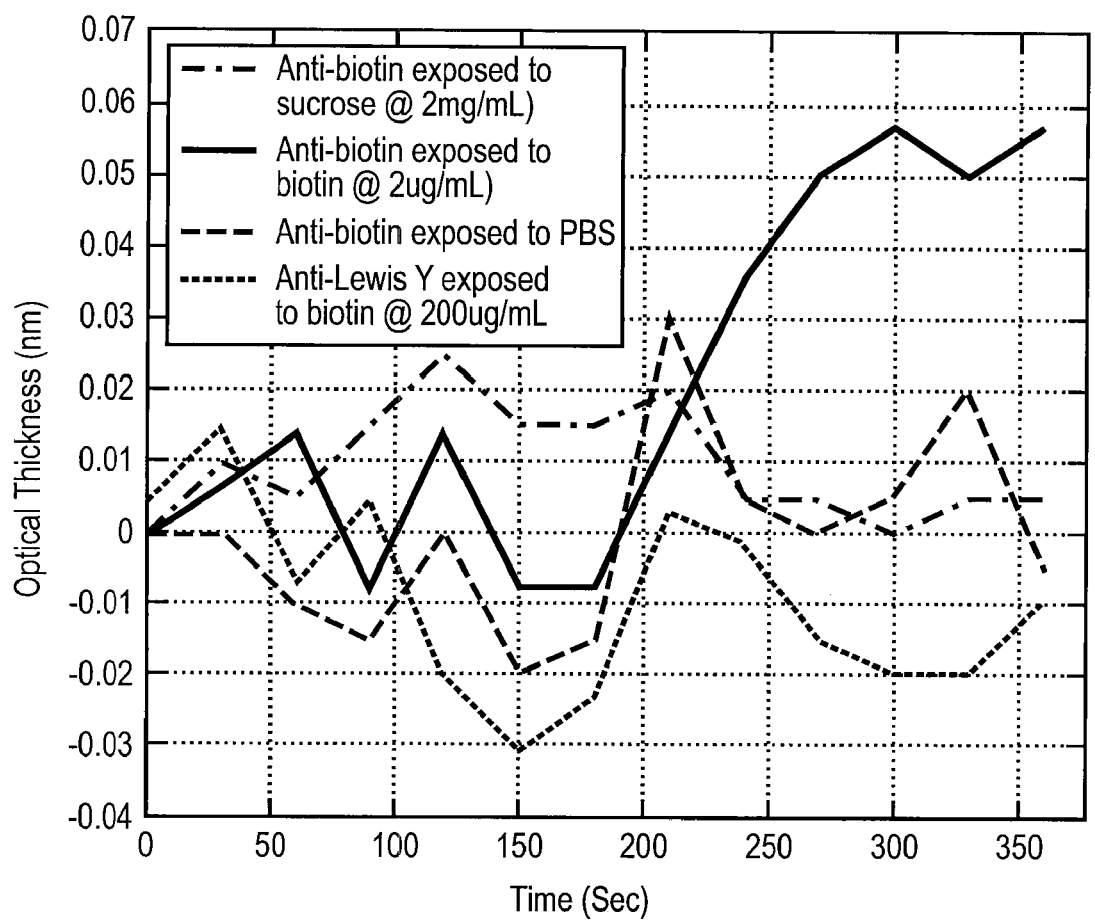
FIG. 10 shows a small molecule binding to a large molecule, negative controls and the base line measurement.

The first fiber was exposed to a solution of 200 µg/mL biotin (Pierce Biotechnology, Rockford Ill.; cat # 29129) in PBS. Controls using a solution of sucrose (Sigma-Aldrich Chemical Company, St Louis, Mo.; cat # S8501) (2 mg/mL) and PBS were carried out on the second and the third fibers to determine baseline noise. Data from these tests are shown in FIG. 10. Biotin binding is seen as an increase in optical thickness, whereas exposure to sucrose shows no detectable increase over baseline (PBS).

Another negative control was carried out using an irrelevant antibody (anti-Lewis Y antibody from Calbiochem, San Diego Calif.; cat# 434636) immobilized in an identical fashion to the anti-biotin antibody above. This immobilized antibody was exposed to a solution of 200 µg/mL biotin. The lack of biotin binding to this antibody indicates that the biotin binding to the anti-biotin antibody is a result of specific interactions and not due to non-specific binding.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

What is claimed is:

1. A disposable detector tip comprising:
   an optical fiber section having a proximal end and a distal end;
   a first reflecting surface formed on the distal end of the optical fiber, the first reflecting surface binding analyte binding molecules;

a second reflecting surface formed on the distal end of the optical fiber proximal to the first reflecting surface, the reflecting surfaces positioned so that light coupled into the proximal end of the optical fiber section is reflected in a manner that results in an interference signal as analyte binds to the analyte binding molecules; and a connector structure including a bore into which the optical fiber section is attached, the connector structure for sliding over a ferrule containing one or more optical fibers for removably attaching the disposable detector tip to the ferrule, the connector structure including arms for holding a proximal end of the optical fiber section in place relative to a distal end of the one or more optical fibers in the ferrule while reducing sensitivity to lateral misalignment.

2. The disposable detector tip of claim 1 where the analyte binding molecules form a layer on a tip of the distal end of the optical fiber section, the layer being exposed to a solution when the distal end of the optical fiber section is immersed in the solution.

3. The disposable detector tip of claim 1 where the first and second reflecting surfaces are separated by at least 50 nm.

4. The disposable detector tip of claim 1, where the connector structure, when attached to the ferrule, maintains a gap between the proximal end of the optical fiber section and the distal end of the one of more optical fibers contained in the ferrule.

5. The disposable detector tip of claim 4 where the gap is less than 100 nm.

6. The disposable detector tip of claim 4 where the gap is between 2 μm and 5 mm.

7. The disposable detector tip of claim 4 where the connector structure includes a flat engagement surface that is approximately flush with the proximal end of the optical fiber section, and contact of the flat engagement surface with the ferrule maintains the gap between the proximal end of the optical fiber section and the one or more optical fibers contained in the ferrule.

8. The disposable detector tip of claim 1 where the ferrule is an SMA ferrule.

9. The disposable detector tip of claim 1 where the arms of the connector structure comprise:

flexible gripping arms for sliding over the ferrule and maintaining enough frictional force on the ferrule to hold the optical fiber section in position relative to the one or more optical fibers in the ferrule.

10. The disposable detector tip of claim 1 where the connector structure can be attached and detached from the ferrule by hand.

11. The disposable detector tip of claim 1 where the one or more optical fibers contained in the ferrule comprise:

one or more input optical fibers and one or more output optical fibers, where the one or more input optical fibers and the one or more output optical fibers are arranged symmetrically about a central axis.

12. The disposable detector tip of claim 1 where the one or more optical fibers contained in the ferrule comprise:

exactly one input optical fiber; and two or more output optical fibers, arranged in a pattern centered about the input optical fiber.

13. The disposable detector tip of claim 1 where the optical fiber section comprises a multimode fiber.

14. The disposable detector tip of claim 1 where the ferrule is integrated in a tip connector assembly for removably attaching to one or more of the disposable detector tips.

15. The disposable detector tip of claim 1 where the tip connector assembly is optically coupled to a source fiber assembly containing one or more source optical fibers via a source connector assembly that is optically coupled to a light source.

16. The disposable detector tip of claim 1 where the tip connector assembly is optically coupled to a detector connector assembly containing one or more detector optical fibers via a detector connector assembly that is optically coupled to a light detector unit that analyzes the interference signal.

17. A method for using a disposable detector tip, the tip including an optical fiber section having a proximal end and a distal end, a first reflecting surface formed on the distal end of the optical fiber, the first reflecting surface binding analyte binding molecules, and a second reflecting surface formed on the distal end of the optical fiber proximal to the first reflecting surface, the reflecting surfaces positioned so that light coupled into the proximal end of the optical fiber section is reflected in a manner that results in an interference signal, comprising:

sliding a connector structure of the disposable detector tip over a ferrule containing one or more optical fibers, the connector structure including a bore into which the optical fiber section is attached;

removably attaching the connector structure to the ferrule using arms for holding a proximal end of the optical fiber section in place relative to a distal end of the one or more optical fibers in the ferrule while reducing sensitivity to lateral misalignment;

immersing the optical fiber section of the disposable detector tip into an analyte solution; and detecting the interference signal that results as analyte binds to the analyte binding molecules.

18. The method of claim 17 where detecting the interference signal further comprises detecting the interference signal resulting from a small molecule-protein binding reaction.

19. The method of claim 17 where detecting the interference signal further comprises detecting the interference signal resulting from a kinetics analysis of molecular interactions.

20. The method of claim 17 where detecting the interference signal further comprises detecting the interference signal from an affinity analysis of molecular interactions.

* * * * *